(12) United States Patent
Bezwada

(10) Patent No.: US 8,309,132 B2
(45) Date of Patent: Nov. 13, 2012

(54) BIOABSORBABLE POLYESTERAMIDES AND USES THEREOF

(75) Inventor: Rao S. Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 616 days.

(21) Appl. No.: 12/466,709

(22) Filed: May 15, 2009

(65) Prior Publication Data

US 2009/0285896 A1 Nov. 19, 2009

Related U.S. Application Data

(60) Provisional application No. 61/053,950, filed on May 16, 2008.

(51) Int. Cl.
*A61K 9/14* (2006.01)
*C08G 69/08* (2006.01)

(52) U.S. Cl. .................... 424/486; 528/310; 528/327

(58) Field of Classification Search .................. None
See application file for complete search history.

(56) References Cited

U.S. PATENT DOCUMENTS

| 2,386,454 | A | 10/1945 | Frosch |
| --- | --- | --- | --- |
| 3,025,323 | A | 3/1962 | Rose |
| 3,044,942 | A | 7/1962 | Baptist |
| 3,297,033 | A | 1/1967 | Schmitt |
| 3,371,069 | A | 2/1968 | Miyamae |
| 3,531,561 | A | 9/1970 | Trehu |
| 3,636,956 | A | 1/1972 | Schneider |
| 4,052,988 | A | 10/1977 | Doddi |
| 4,226,243 | A | 10/1980 | Jamiolkowski et al. |
| 4,343,931 | A | 8/1982 | Barrows |
| 5,902,874 | A | 5/1999 | Roby |
| 5,914,387 | A | 6/1999 | Roby |
| 5,919,893 | A | 7/1999 | Roby |
| 6,120,788 | A | 9/2000 | Barrows |
| 2003/0050422 | A1* | 3/2003 | Bezemer et al. ............... 528/44 |
| 2006/0188547 | A1* | 8/2006 | Bezwada ................... 424/426 |

OTHER PUBLICATIONS

Hollister (nature materials vol. 4 (Jul. 2005)).*
Botines et al. (Journal of Applied POlymer Science, vol. 102, 5545-5558 (2006)).*
Gutowska et al, J. Biomater. Res., 29, 811-21 (1995).
Hoffman, J. Controlled Release, 6, 297-305 (1987).
Mikos et al, Biomaterials, 14, 323-329 (1993).
Schugens et al, J. Biomed. Mater. Res., 30, 449-462 (1996).
Bulletin of the Material Research Society, Special Issue on Tissue Engineering (Guest Editor: Joachim Kohn), 21 (11), 22-26 (1996).

* cited by examiner

*Primary Examiner* — Patricia A Duffy
*Assistant Examiner* — Garen Gotfredson
(74) *Attorney, Agent, or Firm* — Vance Intellectual Property, PC

(57) ABSTRACT

Novel biodegradable polyesteramides derived from optionally functionalized diacids and optionally functionalized diamines or from compounds having both optionally functionalized acid and optionally functionalized amine moieties, their preparation, and absorbable surgical articles fabricated therefrom, such as monofilament and multifilament sutures, films, sheets, plates, clips, staples, pins, screws, stents, stent coatings, packaging materials, and other implantable surgical devices, and the like, are described herein.

16 Claims, No Drawings

BIOABSORBABLE POLYESTERAMIDES AND USES THEREOF

CROSS REFERENCE TO RELATED APPLICATIONS

This application claims the benefit of U.S. Provisional Application Ser. No. 61/053,950, filed May 16, 2008, the disclosure of which is hereby incorporated herein by reference in its entirety.

FIELD OF THE INVENTION

Absorbable polyesteramides derived from optionally functionalized diacids and optionally functionalized diamines or from compounds having both optionally functionalized acid and optionally functionalized amine moieties, their preparation, and absorbable surgical articles fabricated therefrom, such as monofilament and multifilament sutures, films, sheets, plates, clips, staples, pins, screws, stents, stent coatings, and the like, are described herein.

BACKGROUND OF THE INVENTION

Polyesteramides are polymers containing both ester linkages and amide linkages. Their significance to the technology of medical devices stems from the fact that the susceptibility of their ester linkages to hydrolysis confers upon them the ability to be eventually absorbed or resorbed by a body into which they have been implanted and their amide linkages confer upon them the desirable mechanical properties characteristic of polyamides.

Certain fiber-forming polyesteramides obtained from the single stage reaction of approximately equimolar amounts of a monoalkanolamine and a dicarboxylic acid are described, for example, in U.S. Pat. No. 2,386,454.

Other polyesteramides, disclosed in U.S. Pat. No. 4,226,243, have been indicated to be useful for the manufacture of absorbable suture and other surgical devices. These polyesteramides are obtained from the reaction of a dicarboxylic acid ester with a bis-oxyamidodiol, the latter of which is derived from the reaction of diethyl oxalate with a monoalkanolamine, such as ethanolamine.

U.S. Pat. No. 4,343,931 discloses absorbable surgical devices manufactured from polyesteramides which are obtained in a multi-step process by first reacting a diamine with lactic or glycolic acid to produce a diamidediol, and subsequently reacting the diamidediol with a bischloroformate or a compound selected from the group consisting of dicarboxylic acids, diacidchlorides, and dicarboxylic acid dianhydrides to provide the polyesteramide compounds.

U.S. Pat. No. 3,025,323 describes water-soluble amide diols derived from lactone monomers and monoalkanol amines that may be used as intermediates in the preparation of polymers. These intermediates are also disclosed as being useful as sizing additives for paper, leather, or other porous materials.

U.S. Pat. No. 6,120,788 describes fiber-forming bioabsorbable polyesteramides made by the polymerization of diamide diols with 3,6-dioxaoctanedioic acid. Certain of these polymers are said to be useful for the production of surgical sutures having performance characteristics that may include low bending stiffness. They are also disclosed as being useful in the production of other fiber-based bioabsorbable implants and molded devices.

U.S. Pat. No. 5,902,874 describes cyclic monomer derived polyesteramides, which are disclosed as being useful for manufacture into shaped articles for use, for example, as surgical devices.

U.S. Pat. No. 5,914,387 describes shaped articles which are prepared from polyesteramides and which are disclosed as being useful as surgical devices. The disclosed polyesteramides have amino acid-derived groups alternating with hydroxy acid-derived groups.

U.S. Pat. No. 5,919,893 describes polyesteramides which are disclosed as being suitable for use in biomedical applications and which may be obtained by reacting a diamino alkyl ester with an alpha-hydroxy acid to form a diamide diol which may be further reacted with an acyl halide or dicarboxylic acid to provide the polyesteramide.

Shaped articles made from nylon have been widely accepted for a variety of applications, including some biomedical applications. Generally speaking, nylon refers to a family of high strength, resilient synthetic polymeric materials containing recurring amide groups in the polymer backbone. While nylon polymers have certain useful properties, shaped articles based on nylon are not typically bioabsorbable and may therefore be unacceptable in circumstances that require bioabsorption. For example, certain biomedical applications, such as surgical devices including but not limited to monofilament and multifilament sutures, films, sheets, plates, clips, staples, pins, screws, stents, stent coatings, and the like, require a material that is bioabsorbable.

In addition, high strength, highly flexible, tough, and durable fibers that possess a prolonged flex fatigue life are needed for use as braided, knitted, woven, or non-woven implants to augment and/or temporarily reinforce autologous tissue grafts or to serve as scaffolds for tissue regeneration. One example of such an implant is known as a ligament augmentation device (LAD) used to reconstruct the anterior cruciate ligament (ACL) of the knee. Bioabsorbable fibers of the prior art, such as poly(L-lactic acid) (PLA), have not been successful in this application due to low flex fatigue life, shedding of wear debris due to the brittle nature of the fibers, and prolonged bioabsorption time.

Other well known uses for bioabsorbable polymers that have not been fully realized or perfected with available polymers of the prior art include scaffolds for tissue engineering, bioabsorbable knitted vascular grafts, drug-releasing devices, growth factor-releasing implants for bone and tissue regeneration, and fiber-reinforced composites for orthopedic applications. For example, composites of polymers reinforced with dissimilar materials, such as dissolvable glass fiber reinforced poly(lactic acid) are generally unacceptable for use as implants. Although dissolvable glass fibers provide high modulus needed for the composite to have high initial strength and stiffness, adhesion between glass and polymer may invariably fail prematurely in vivo resulting in devices with unacceptable in vivo performance.

Self-reinforced composites were developed as an alternative to composites of polymers reinforced with dissimilar materials, such as those described above. In self-reinforced fiber composites, both reinforcing fibers and matrix are generally made of the same material. Although the stiffness is lower than can be achieved with glass fibers, this alternative type of composite ensures good adhesion between fiber and matrix and thus may offer the possibility of longer lasting in vivo strength. Self-reinforced poly(glycolic acid) (PGA) rods, pins and screws made by hot pressing or sintering PGA fibers have shown promise in clinical use. The main disadvantage of PGA in general is that it typically degrades at too fast a rate for orthopedic applications and releases an excessive concentration of acidic degradation products into the surrounding tissue.

Despite advancements in the art of producing polymeric materials and methods for making polymeric materials suitable for use in sutures, molded devices, and similar surgical articles, presently available polymers generally lack adequate performance properties desirable in surgical articles, for example, those related to bioabsorption, flex fatigue life, strength in use, flexibility and/or durability. Thus, there continues to be a need for new fibers that are monofilament, have high initial tensile knot strength, retain useful strength in vivo for a period of time, for example, about two weeks or longer, are fully bioabsorbed within a few months after strength loss, and have very low bending stiffness. There is also a need for surgical article materials that have strength and resiliency characteristics comparable to that of nylon, but which are also bioabsorbable. It would be particularly advantageous to provide surgical article materials having tunable physical and/or biological properties, so that surgical articles having a variety of end uses can be prepared. The present invention is related to these and other important ends.

SUMMARY OF THE INVENTION

Accordingly, the present invention is directed, in part, to polyesteramides which are derived from optionally functionalized diacids and optionally functionalized diamines and which have tunable physical and/or biological properties. In one embodiment, the polyesteramides comprise Formula I:

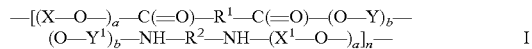

wherein:
each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
each X and $X^1$ is independently —C(=O)—CH(CH$_3$)—, —C(=O)—(CH$_2$)$_y$—, or —C(=O)—(CH$_2$CH$_2$O)$_z$—CH$_2$—;
each Y and $Y^1$ is independently —CH(CH$_3$)—C(=O)—; —(CH$_2$)$_y$—C(=O)—; or —(CH$_2$CH$_2$O)$_z$—CH$_2$—C(=O)—;
each a and b is independently an integer from about 1 to about 6;
each y and z is independently an integer from about 1 to about 24; and
n is an integer from about 5 to about 5000.

In another embodiment, the invention is directed to polyesteramides comprising Formula IV:

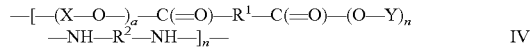

wherein:
each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
each X is independently —C(=O)—CH(CH$_3$)—, —C(=O)—(CH$_2$)$_y$—, or —C(=O)—(CH$_2$CH$_2$O)$_z$—CH$_2$—;
each Y is independently —CH(CH$_3$)—C(=O)—; —(CH$_2$)$_y$—C(=O)—; or —(CH$_2$CH$_2$O)$_z$—CH$_2$—C(=O)—;
each a and b is independently an integer from about 2 to about 6;
each y and z is independently an integer from about 1 to about 24; and
n is an integer from about 5 to about 1000.

In yet another embodiment, the present invention is directed to polyesteramides comprising Formula VI:

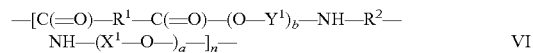

wherein:
each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
each $X^1$ is independently —C(=O)—CH(CH$_3$)—, —C(=O)—(CH$_2$)$_y$—, or —C(=O)—(CH$_2$CH$_2$O)$_z$—CH$_2$—;
each $Y^1$ is independently —CH(CH$_3$)—C(=O)—, —(CH$_2$)$_y$—C(=O)—, or —(CH$_2$CH$_2$O)$_z$—CH$_2$—C(=O)—;
each a and b is independently an integer from about 1 to about 6;
each y and z is independently an integer from about 1 to about 24; and
n is an integer from about 5 to about 5000.

The present invention is also directed, in part, to polyesteramides which are derived from compounds having both optionally functionalized acid and optionally functionalized amine moieties and which have tunable physical and/or biological properties. In certain embodiments, the invention is directed to polyesteramides comprising Formula VIII:

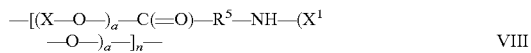

wherein:
each $R^5$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(═O)—O— or —O—C(═O)—;
each X and $X^1$ is independently —C(═O)—CH($CH_3$)—, —C(═O)—($CH_2$)$_y$—, or —C(═O)—($CH_2CH_2O$)$_z$—$CH_2$—;
each a is independently an integer from about 1 to about 6;
each y and z is independently an integer from about 1 to about 24; and
n is an integer from about 5 to about 5000.

In yet another embodiment, the invention relates to polyesteramides comprising Formula XI:

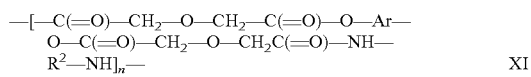

wherein:
each Ar is arylene;
each $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(═O)—O— or —O—C(═O)—; and
n is an integer from about 5 to about 5000.

In still another embodiment, the invention is directed to polyesteramides comprising:
a polymer wherein:
one or more of the amido linkages in the polymer backbone are replaced with —[C(═O)—(O—$X^1$)$_a$—N]— linkages; or
one or more of the ester linkages in the polymer backbone are replaced with —[C(═O)—(O—$X^2$)$_b$—O]— linkages;
wherein:
each $X^1$ and each $X^2$ is independently chosen from: —CH($CH_3$)—C(═O)—, —($CH_2$)$_y$—C(═O)— or —($CH_2CH_2O$)$_z$—$CH_2$—C(═O)—; and each a and each b is independently an integer from 1 to about 24, provided that at least one a or at least one b is an integer from 2 to about 24.

In another embodiment, the invention is directed to surgical articles, coatings for stents, delivery systems for one or more biologically or pharmacologically active agents, and/or biodegradable packaging materials, each comprising the polyesteramides of the present invention as disclosed herein.

DETAILED DESCRIPTION OF ILLUSTRATIVE EMBODIMENTS

The present invention relates to the discovery of new biodegradable polyesteramides. In certain embodiments, the polyesteramides are derived from functionalized diacids and/or functionalized aliphatic diamines. In other embodiments, the polyesteramides are derived from monomers having optionally functionalized acid and optionally functionalized amine moieties.

As employed above and throughout the disclosure, the following terms, unless otherwise indicated, shall be understood to have the following meanings.

As used herein, "alkyl" refers to an optionally substituted, saturated straight, or branched hydrocarbon moiety having from about 1 to about 20 carbon atoms (and all combinations and subcombinations of ranges of carbon atoms and specific numbers of carbon atoms therein), preferably with from about 1 to about 8 carbon atoms, herein referred to as "lower alkyl", more preferably from about 1 to about 3 carbon atoms, with methyl being even more preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, the term "aryl" refers to an optionally substituted, mono-, di-, tri-, or other multicyclic aromatic ring system moiety having from about 6 to about 50 carbon atoms (and all combinations and subcombinations of ranges of carbon atoms and specific numbers of carbon atoms therein), preferably with from about 6 to about 10 carbons, with about 6 carbon atoms being preferred. Non-limiting examples include, for example, phenyl, naphthyl, anthracenyl, and phenanthrenyl.

As used herein, the term "cycloalkyl" refers to an optionally substituted, mono-, di-, tri-, or other multicyclic alicyclic ring system moiety having from about 3 to about 20 carbon atoms (and all combinations and subcombinations of ranges of carbon atoms and specific numbers of carbon atoms therein). In some preferred embodiments, the cycloalkyl groups have from about 3 to about 8 carbon atoms, more preferably from about 3 to about 6 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "alkylene" refers to a bivalent alkyl moiety having the general formula —($CH_2$)$_n$—, where n is from about 1 to about 150, preferably about 1 to about 20, more preferably about 1 to about 16, with about 1 to about 10 being even more preferred. By bivalent, it is meant that the group has two open sites each of which bonds to another group. Non-limiting examples include methylene, ethylene, trimethylene, pentamethylene, and hexamethylene. Alkylene groups can be optionally substituted with alkyl, wherein alkyl is as previously defined. The term "lower alkylene" herein refers to those alkylene groups having from about 1 to about 6 carbon atoms.

As used herein, "arylene" refers to a bivalent aryl moiety, wherein aryl is as previously defined. The ring system may be monocyclic or fused polycyclic (e.g., bicyclic, tricyclic, etc.). A $C_6$ ring system, i.e., a phenylene ring, is a preferred aryl group. In various embodiments, the bivalent $C_6$aryl moiety may be a 1,2-, 1,3-, or 1,4-bivalent aryl moiety.

As used herein, "cycloalkylene" refers to a bivalent cycloalkyl moiety, wherein cycloalkyl is as previously defined. Cycloalkylene is a type of alkylene group which is a cycloalkyl group with two open bonding sites.

As used herein, "cycloalkylenealkylene" refers to a bivalent moiety, wherein a cycloalkylene group is bonded to a non-cyclic alkylene group, wherein each of the cycloalkylene and non-cyclic alkylene groups has one open bonding site, and wherein cycloalkylene and alkylene are each as previously defined. "Cycloalkylenealkylene" includes moieties having -cycloalkylene-alkylene- and -alkylene-cycloalkylene-bonding orders or configurations.

As used herein, "arylenealkylene" refers to a bivalent moiety, wherein an arylene group is bonded to a non-cyclic alkylene group, and each of the arylene and non-cyclic alkylene group has one open bonding site, wherein arylene and alkylene are each as previously defined. "Arylenealkylene" includes moieties having -arylene-alkylene- and -alkylene-arylene-bonding orders or configurations.

As used herein, "arylenealkylenearylene" refers to bivalent moieties, wherein two arylene groups are bonded to a non-cyclic alkylene group, and each of the arylene groups has one open bonding site, wherein arylene and alkylene are each as previously defined.

As used herein, "cycloalkylenealkylenecycloalkylene" refers to a bivalent moiety, wherein two cycloalkylene groups are bonded to a non-cyclic alkylene group, and each of the cycloalkylene groups has one open bonding site, wherein cycloalkylene and alkylene are each as previously defined.

As used herein, "arylenealkylenecycloalkylene" refers to a bivalent moiety, wherein an arylene and a cycloalkylene group are each bonded to a non-cyclic alkylene group, and each of the arylene and cycloalkylene groups has one open bonding site, wherein arylene, cycloalkylene, and alkylene are as previously defined. "Arylenealkylenecycloalkylene" includes moieties having -arylene-alkylene-cycloalkylene- and cycloalkylene-alkylene-arylene-bonding orders or configurations.

When any variable occurs more than one time in any constituent or in any formula, its definition in each occurrence is independent of its definition at every other occurrence. Combinations of substituents and/or variables are permissible only if such combinations result in stable compounds. Within the context of the present invention, compounds are stable if they do not degrade significantly prior to their intended use under normal conditions. In some instances, compounds of the invention may be designed or required to be bioabsorbed or biodegraded as part of their intended function. Bioabsorbability and/or biodegradability, which may be an advantageous property of the present polymers, is not intended to mean that the polymeric compound are unstable.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form, except where such limit is clearly defined.

Accordingly, in one embodiment of the present invention, there are provided polyesteramides comprising Formula I:

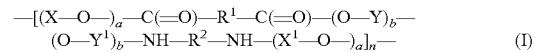

(I)

wherein:

each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:

(1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;

each X and $X^1$ is independently —C(=O)—CH(CH$_3$)—, —C(=O)—(CH$_2$)$_y$— or —C(=O)—(CH$_2$CH$_2$O)$_z$—CH$_2$—;

each Y and $Y^1$ is independently —CH(CH$_3$)—C(=O)—, —(CH$_2$)$_y$—C(=O)— or —(CH$_2$CH$_2$O)$_z$—CH$_2$—C(=O)—;

each a and b is independently an integer from about 1 to about 6;

each y and z is independently an integer from about 1 to about 24; and n is an integer from about 5 to about 5000.

In certain preferred embodiments, the polyesteramides comprising Formula I may be prepared by the condensation polymerization of functionalized diacids of Formula II and functionalized diamines of Formula III as shown below:

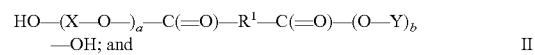

II

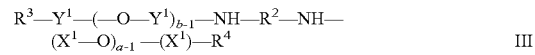

III wherein $R^1$, $R^2$, X, $X^1$, Y, $Y^1$, a and b are each as defined above, and $R^3$ and $R^4$ are independently selected from Cl, F, Br, and I. Suitable examples of diacids of general Formula II which can be used in the present invention include but are not limited to the following:

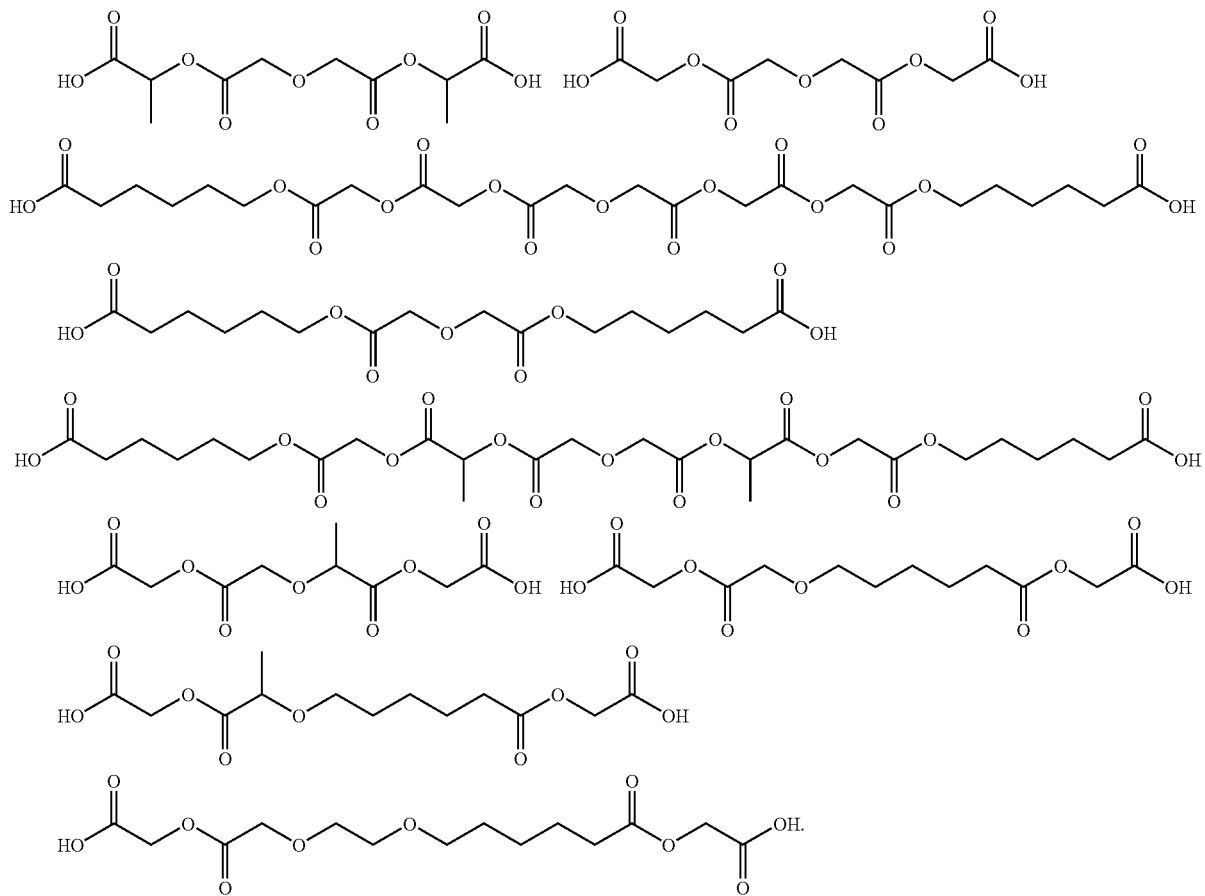

In another embodiment, the present invention provides polyesteramides comprising Formula IV:

$$—[—(X—O—)_a—C(=O)—R^1—C(=O)—(O—Y)_b—NH—R^2—NH—]_n— \quad\quad IV$$

wherein:
each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
each X is independently —C(=O)—CH($CH_3$)—, —C(=O)—$(CH_2)_y$—, or —C(=O)—$(CH_2CH_2O)_z$—$CH_2$—;
each Y is independently —CH($CH_3$)—C(=O)—, —$(CH_2)_y$—C(=O)—, or —$(CH_2CH_2O)_z$—$CH_2$—C(=O)—;
each a and b is independently an integer from about 2 to about 6;
each y and z is independently an integer from about 1 to about 24; and
n is an integer from about 5 to about 5000.

In certain preferred embodiments, the polyesteramides comprising Formula IV may be prepared by the condensation polymerization of functionalized diacids of Formula II and diamines of Formula V as shown below:

$$HO—(X—O—)_a—C(=O)—R^1—C(=O)—(O—Y)_b—OH \quad\quad II$$

$$NH_2—R^2—NH_2 \quad\quad V$$

wherein $R_1$, $R_2$, X, Y, a and b are each as defined above.
In yet another embodiment the present invention provides polyesteramides comprising Formula VI:

$$—[C(=O)—R^1—C(=O)—(O—Y^1)_b—NH—R^2—NH—(X^1—O—)_a—]_n—; \quad\quad VI$$

wherein:
each $R^1$ and $R^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(═O)—O— or —O—C(═O)—;

each $X^1$ is independently —C(═O)—CH(CH$_3$)—, —C(═O)—(CH$_2$)$_y$—, or —C(═O)—(CH$_2$CH$_2$O)$_n$—CH$_2$—;

each $Y^1$ is independently —CH(CH$_3$)—C(═O)—, —(CH$_2$)$_y$—C(═O)—, or —(CH$_2$CH$_2$O)$_z$—CH$_2$—C(═O)—;

each a and b is independently an integer from about 1 to about 6;

each y and z is independently an integer from about 1 to about 24; and n is an integer from about 5 to about 5000.

In some preferred embodiments, polyesteramides comprising Formula VI may be prepared by the condensation polymerization of diacids of Formula VII and functionalized diamines of Formula III as shown below:

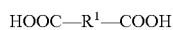  HOOC—R$^1$—COOH  VII

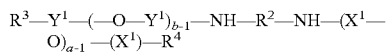  R$^3$—Y$^1$—(—O—Y$^1$)$_{b-1}$—NH—R$^2$—NH—(X$^1$—O)$_{a-1}$—(X$^1$)—R$^4$  III wherein R$^1$, R$^2$, X$^1$, Y$^1$, a and b are each as indicated hereinabove; and R$^3$ and R$^4$ are independently selected from Cl, F, Br, and I.

In some preferred embodiments, the polyesteramides comprising Formula I, IV, or VI have the following formula:

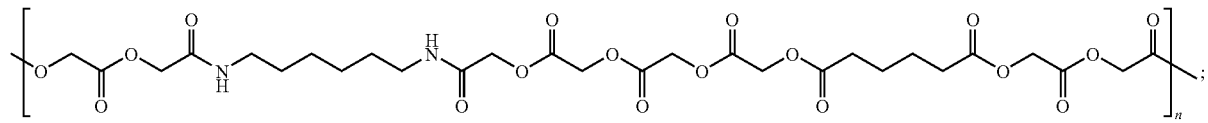

wherein n is as previously defined.

In other preferred embodiments, the polyesteramides comprising Formula I, IV, or VI have the following formula:

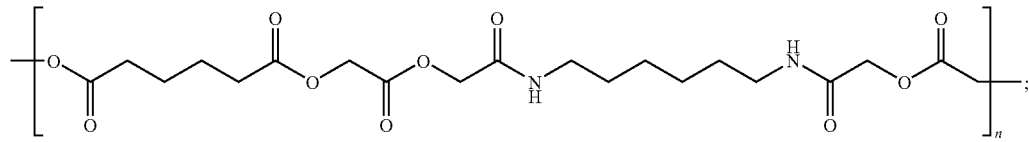

wherein n is as previously defined.

In yet another embodiment the present invention provides polyesteramides comprising: a polymer wherein:

one or more of the amido linkages in the polymer backbone are replaced with —[C(═O)—(O—X$^1$)$_a$—N]— linkages; or one or more of the ester linkages in the polymer backbone are replaced with —[C(═O)—(O—X$^2$)$_b$—O]— linkages;

wherein:
each $X^1$ and each $X^2$ is independently selected from: —CH(CH$_3$)—C(═O)—, —(CH$_2$)$_y$—C(═O)— and —(CH$_2$CH$_2$O)$_z$—CH$_2$—C(═O)—; and each a and each b is independently an integer from 1 to about 24, provided that at least one a or at least one b is an integer from 2 to about 24. Preferably, one or more of the amido linkages in the polymer backbone are replaced with —[C(═O)—(O—X$^1$)$_a$—N]— linkages; and one or more of the ester linkages in the polymer backbone are replaced with —[C(═O)—(O—X$^2$)$_b$—O]— linkages. Alternatively preferred polyesteramides contain one or more ester linkages in the polymer backbone replaced with —[C(═O)—(O—X$^2$)$_b$—O]— linkages, wherein each a and each b is independently an integer from 1 to about 12, more preferably 1 to about 6, with from 1 to about 3 being even more preferred. Other alternatively preferred polyesteramides contain one or more amido linkages in the polymer backbone replaced with —[C(═O)—(O—X$^1$)$_a$—N]— linkages, wherein each a and each b is independently an integer from 1 to about 12, more preferably 1 to about 6, with from 1 to about 3 being even more preferred.

Suitable examples of diacids of general Formula VII which may be useful in the preparation of the polyesteramides of the present invention include but are not limited to the following:

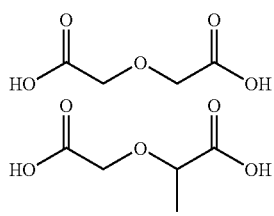

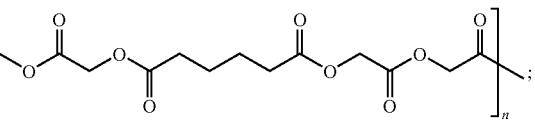

-continued

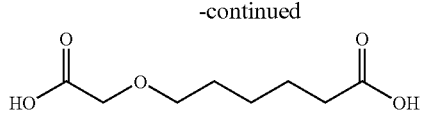

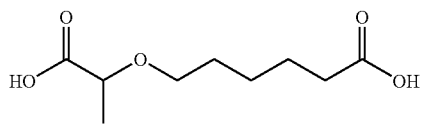

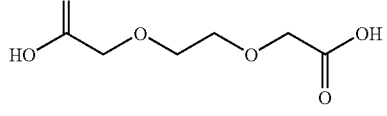

-continued

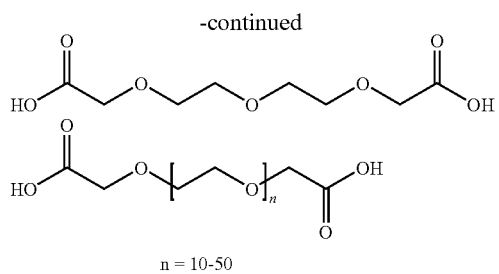

n = 10-50

In certain preferred embodiments of polyesteramides comprising Formula I, IV, or VI, $R^1$ is alkylene, preferably $C_1$-$C_{60}$, more preferably $C_1$-$C_{20}$, even more preferably $C_1$-$C_{16}$, still more preferably $C_1$-$C_{12}$, yet more preferably $C_3$-$C_9$alkylene. Alternatively, the alkylene is preferably $C_3$, $C_6$, $C_7$, $C_9$, or $C_{16}$alkylene. Also in preferred embodiments, alkylene is unsubstituted or substituted with alkyl, preferably $C_1$-$C_3$alkyl, more preferably methyl. In other preferred embodiments wherein one or more —(CH$_2$)— moieties in the alkylene chain portion of $R^1$ are replaced with a heteroatom, preferably —O— or —S—, with —O— being more preferred. Preferably, one or more —(CH$_2$)— moieties in the alkylene chain portion of $R^1$ are replaced with from about 1 to about 50 —O— or —S— atoms, more preferably from about 10 to about 50 —O— or —S— atoms. In other alternative embodiments, wherein one or more —(CH$_2$)-moieties in the alkylene chain portion of $R^1$ are replaced, they are preferably replaced with from about 1 to about 10 —O— or —S— atoms, more preferably from about 1 to about 5 —O— or —S— atoms, still more preferably from about 1 to about 3 —O— or —S— atoms.

In other preferred embodiments of polyesteramides comprising Formula I, IV, or VI, wherein $R^1$ is alkylene and one or more —(CH$_2$CH$_2$)— moieties in the alkylene chain portion of $R^1$ are replaced, they are preferably replaced with from about 1 to about 10 —O—C(=O)— or —C(=O)—O— moieties, more preferably from about 1 to about 8 —O—C(=O)— or —C(=O)—O— moieties, still more preferably from about 2 to about 6 —O—C(=O)— or —C(=O)—O— moieties.

In certain preferred embodiments of polyesteramides comprising Formula I, IV, or VI, $R^2$ is alkylene or arylenealkylenecycloalkylene, more preferably arylenealkylenecycloalkylene. In embodiments wherein $R^2$ is alkylene, the alkylene is preferably $C_1$-$C_{150}$, more preferably $C_5$-$C_{50}$, still more preferably $C_{10}$-$C_{20}$, still more preferably $C_{10}$-$C_{18}$, yet more preferably $C_{10}$-$C_{14}$alkylene. In some more preferred embodiments, the alkylene is unsubstituted or substituted with alkyl, preferably $C_1$-$C_3$alkyl, more preferably methyl. In other preferred embodiments wherein one or more —(CH$_2$)-moieties in the alkylene chain portion of $R^2$ are replaced with a heteroatom, such as —O— or —S—, preferably —O—, they are preferably replaced with from about 1 to about 50 —O— or —S— atoms, more preferably from about 10 to about 50 —O— or —S— atoms. In other alternative embodiments, wherein one or more —(CH$_2$)-moieties in the alkylene chain portion of $R^5$ are replaced with —O— or —S— atoms, preferably —O— atoms, they are preferably replaced with from about 1 to about 10 —O— or —S— atoms, more preferably from about 1 to about 5 —O— or —S— atoms, still more preferably from about 1 to about 3 —O— or —S— atoms.

In other preferred embodiments of polyesteramides comprising Formula I, IV, or VI, wherein $R^2$ is alkylene and one or more —(CH$_2$CH$_2$)— moieties in the alkylene chain portion of $R^2$ are replaced, they are preferably replaced with from about 1 to about 10 —O—C(=O)— or —C(=O)—O— moieties, more preferably from about 1 to about 8, still more preferably from about 2 to about 6 —O—C(=O)— or —C(=O)—O— moieties.

In certain preferred embodiments of polyesteramides comprising Formulas I, IV, VI or VIII or intermediates thereof comprising Formulas II, III or IX, each X and/or $X^1$ are independently —C(=O)—CH(CH$_3$)— or —C(=O)—(CH$_2$)$_y$—. In other preferred embodiments; each X and/or $X^1$ is independently —C(=O)—(CH$_2$CH$_2$O)$_z$—CH$_2$—. Alternatively preferred, each X and/or $X^1$ is independently —C(=O)—CH(CH$_3$)—, —C(=O)—(CH$_2$)—, —C(=O)—(CH$_2$)$_5$—, or —C(=O)—CH$_2$CH$_2$OCH$_2$—.

In other preferred embodiments of polyesteramides comprising Formulas I, IV, or VI or intermediates thereof comprising Formulas II or III, each Y and/or $Y^1$ is independently —CH(CH$_3$)—C(=O)—, —(CH$_2$)$_y$—C(=O)—In other preferred embodiments; each Y and/or $Y^1$ is independently —(CH$_2$CH$_2$O)$_z$—CH$_2$—C(=O)—. Alternatively preferred, each Y and/or $Y^1$ is independently —CH(CH$_3$)—C(=O)—, —(CH$_2$)—C(=O)—, —(CH$_2$)$_5$—C(=O)— or —CH$_2$CH$_2$O—CH$_2$—C(=O)—.

In certain preferred embodiments of polyesteramides comprising Formula VIII or intermediates thereof comprising Formula IX, $R^5$ is alkylene or arylenealkylenearylalkylene. In embodiments wherein $R^5$ is alkylene or contains an alkylene moiety, such as in the group arylenealkylenearylalkylene, the alkylene or alkylene portion is preferably $C_1$-$C_{150}$, more preferably $C_5$-$C_{50}$, still more preferably $C_{10}$-$C_{20}$, still more preferably $C_{10}$-$C_{18}$, yet more preferably $C_{10}$-$C_{14}$alkylene. In some more preferred embodiments, the alkylene portion is unsubstituted or substituted with alkyl, preferably $C_1$-$C_3$alkyl, more preferably methyl. In other preferred embodiments wherein one or more —(CH$_2$)-moieties in the alkylene chain portion of $R^5$ are replaced, they are preferably replaced with one or more heteroatoms, for example —O— or —S—, preferably —O—, with about 1 to about 50 —O— atoms being preferred, more preferably from about 10 to about 50 —O— atoms. In other alternative embodiments, wherein one or more —(CH$_2$)— moieties in the alkylene chain portion of $R^5$ are replaced, they are preferably replaced with from about 1 to about 10 —O— atoms, more preferably from about 1 to about 5, still more preferably from about 1 to about 3 —O— atoms.

In other preferred embodiments of polyesteramides comprising Formula VIII or intermediates thereof comprising Formula IX, wherein $R^5$ is alkylene and one or more —(CH$_2$CH$_2$)— moieties in the alkylene chain portion of $R^5$ are replaced, they are preferably replaced with from about 1 to about 10 —O—C(=O)— or —C(=O)—O— moieties, more preferably from about 1 to about 8 —O—C(=O)— or —C(=O)—O— moieties, still more preferably from about 2 to about 6 —O—C(=O)— or —C(=O)—O— moieties.

In preferred embodiments of polyesteramides comprising Formula VIII or intermediates thereof comprising Formula IX, wherein $R^5$ contains an arylene portion, such as in the group arylenealkylenearylalkylene, the arylene portion is preferably $C_6$arylene.

In other preferred embodiments of polyesteramides comprising Formula I, IV, VI or VIII or intermediates thereof comprising Formula II, III or IX, each a and b is independently an integer from about 1 to about 12, more preferably from about 2 to about 12. Alternatively preferred, each a and b is independently an integer from about 1 to about 6, more preferably from about 2 to about 6. In still other preferred embodiments, each a and b is independently an integer from about 1 to about 3, more preferably from about 2 to about 3.

In some preferred embodiments of polyesteramides comprising Formula I, IV, VI or VIII or intermediates thereof comprising Formula II, III or IX, each y and z is independently an integer from about 1 to about 24, more preferably from about 1 to about 18, still more preferably from about 1 to about 12, yet more preferably from about 1 to about 8, even more preferably from about 1 to about 6. In certain alternatively preferred embodiments, each y and z is independently 1 or 5.

In other preferred embodiments of polyesteramides comprising Formula I, IV, VI, or VIII, n is an integer from about 5 to about 100, more preferably from about 10 to about 50. In certain alternative embodiments, n is an integer from about 5 to about 5000, more preferably from 10 to 3000, still more preferably from 20 to 1000.

In certain embodiments of the invention, polyesteramides comprising Formula I may be prepared by a process that comprises contacting a compound of Formula II:

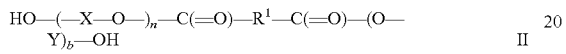

with a compound of Formula III:

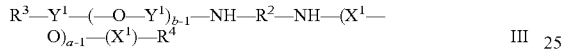

wherein $R^1$, $R^2$, X, $X^1$, Y, and $Y^1$, a and b are each as defined above; and $R^3$ and $R^4$ are independently selected from Cl, F, Br, and I;

for a time and under conditions effective to provide the polyesteramide of Formula I.

In certain embodiments of the invention, polyesteramides comprising Formula IV may be prepared by a process that comprises contacting a compound of Formula II:

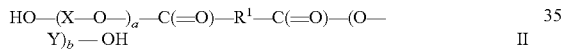

with a compound of Formula V:

wherein $R_1$, $R_2$, X, Y, a and b are each as defined above;

for a time and under conditions effective to provide the polyesteramide of Formula IV.

In certain embodiments of the invention, polyesteramides comprising Formula VI may be provided by a process that comprises contacting a compound of Formula VII:

$$HOOC—R^1—COOH \qquad VII$$

with a compound of Formula III:

wherein $R^1$, $R^2$, $X^1$, $Y^1$, a and b are each as defined above; and $R^3$ and $R^4$ are independently selected from Cl, F, Br, and I;

for a time and under conditions effective to provide the polyesteramide of Formula VI.

In certain embodiments of the invention, polyesteramides comprising Formula VIII may be prepared by a process that comprises contacting a compound of Formula IX:

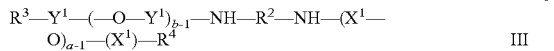

with a compound of Formula IX:

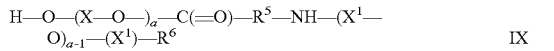

wherein $R^5$, X, $X^1$, and a are each as indicated hereinabove; and $R^6$ is Cl, F, Br, or I;

for a time and under conditions effective to provide the polyesteramide of Formula VIII.

In yet another embodiment, the present invention provides biodegradable polyesteramides comprising Formula VIII:

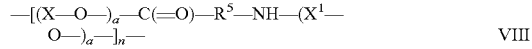

wherein:
each $R^5$ is independently alkylene, cycloalkylenealkylene, arylenealkylene, arylenealkylenearylene, cycloalkylenealkylenecycloalkylene, or arylenealkylenecycloalkylene, wherein:
(1) one or more of the —$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
(2) one or more of the —$CH_2$—$CH_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
each X and $X^1$ is independently —C(=O)—CH($CH_3$)—, —C(=O)—($CH_2$)$_y$—, or —C(=O)—($CH_2CH_2O$)$_z$—$CH_2$—;
each a is independently an integer from about 1 to about 6;
each y and z is independently an integer from about 1 to about 24; and
n is an integer from about 5 to about 5000.

It would be readily apparent to one of ordinary skill in the art once armed with the teachings in the present application that the termini in any of the polyesteramides of the present invention may be determined, in part, by the ratio of reactants employed in preparation of the polyesteramide. It would also be apparent to the ordinarily skilled artisan that the terminal groups for a given polyesteramide may be derivatized by further reacting the polyesteramide with additional derivatizing agents.

In certain preferred embodiments, polyesteramides of Formula VIII are prepared by self-condensation polymerization of amino acids of Formula (IX):

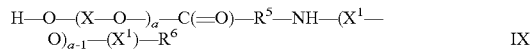

wherein $R^5$, X, $X^1$, and a are each as indicated hereinabove; and $R^6$ is Cl, F, Br, or I.

Alternatively, the polyesteramides of Formula VIII are prepared by self-condensation polymerization of amino acids of Formula (IXa):

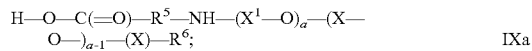

or by self-condensation polymerization of amino acids of Formula (IXb):

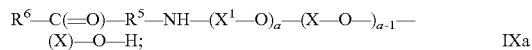

In some embodiments, polyesteramides are provided that are in part derived from a compound of Formula XI:

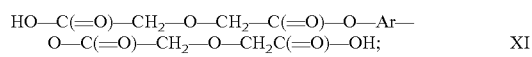

wherein Ar is an arylene moiety that is derived from an aryl-containing compound in which the aryl group is substituted with two hydroxyl groups. In some preferred embodiments, the diacid subunits are derived from diacids prepared by ring opening of diglycolic anhydride with a dihydroxy substituted aryl compound, more preferably a dihydroxy substituted aryl compound selected from the group consisting of natural products such as flavonoids, coumarins, chalcones, acetophenones, or benzophenones, each having the required hydroxy substituents. Non-limiting examples include quercetin, quercetrin, epicatechin, catechin, hesperetin, kaempherol, anthocyanidine, rutin, myricetin, fisetin, isoquercitrin, rhamnetin, and other compounds with at least one dihydroxy substituted aryl subunit. In alternatively preferred embodiments, amino acids such as tyrosine, as well as drugs and/or biologically active compounds may also be used to provide the diacids via opening of the diglycolic anhydride, so long as they contain an aryl group with the required hydroxyl substituents thereon. Other dihydroxy-substituted aryl compounds in addition to those exemplified above would be apparent to one of ordinary skill in the art, once armed with the teachings in the present application.

Suitable diamines of general Formula V which can be used in the present invention include but are not limited to polyethyleneimines, polyoxypropylenediamines available under the tradename JEFFAMINES (Huntsman Corporation, Houston, Tex.), spermine, spermidine, hexamethylenediamine, octamethylenediamine, decamethylene diamine, dodecamethylene diamine, hexadecamethylene diamine, octadecamethylene diamine, polyamidoamine dendrimers, dextrans, PEG-dextran conjugates, cysteines, proteins containing amines, and hydrolysable diamines having the following formulas.

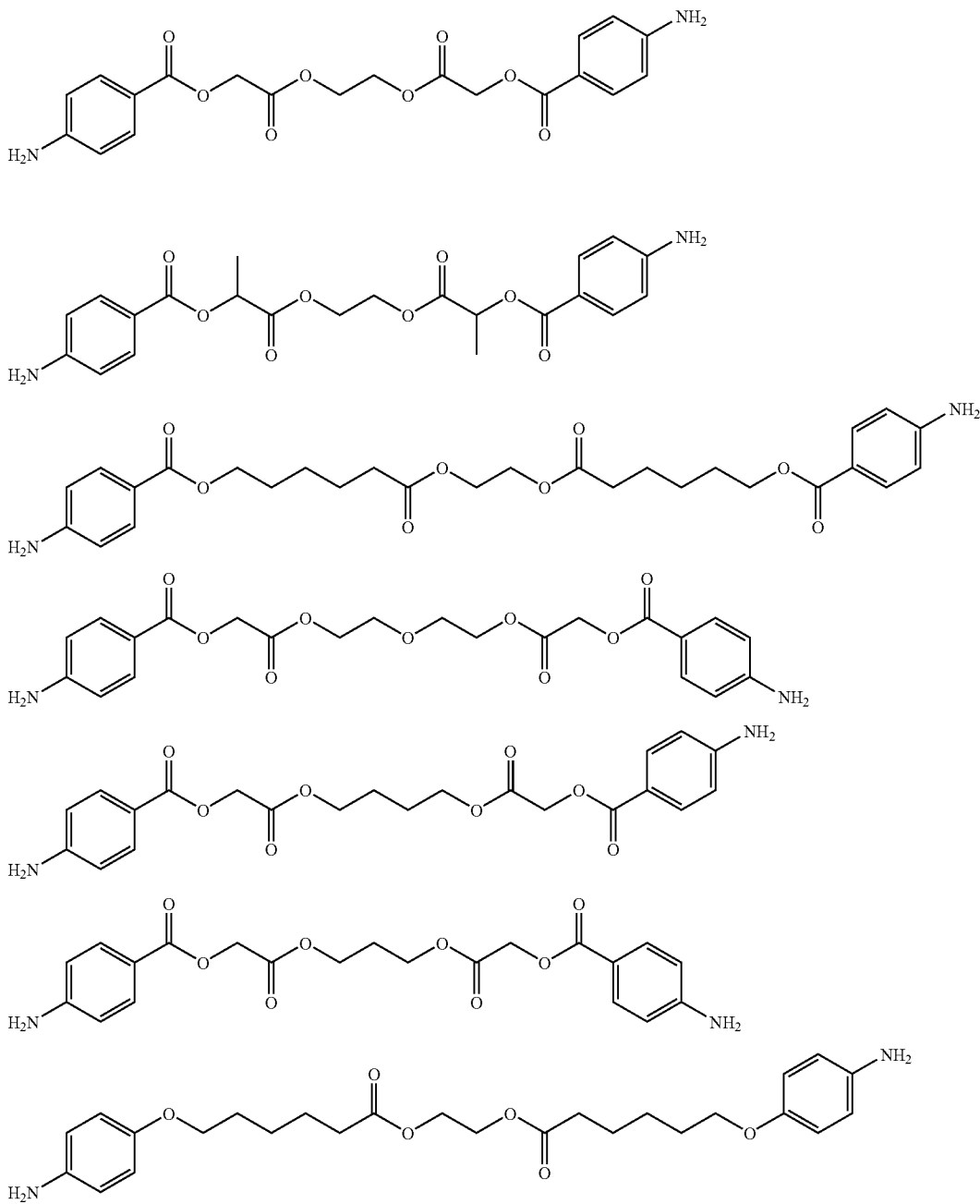

-continued
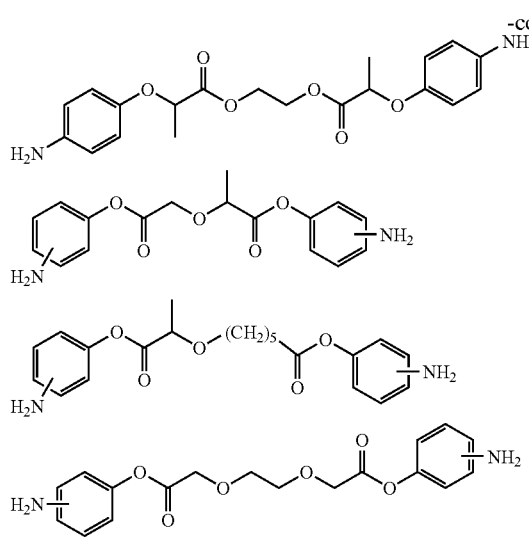
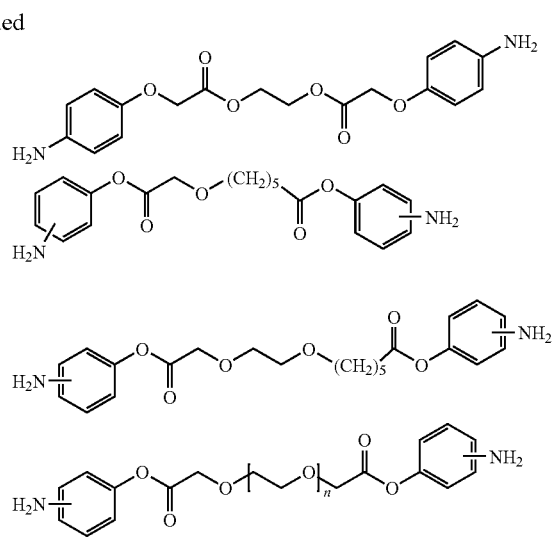
Suitable examples of functionalized diamines of Formula III that can be used in the present invention include but are not limited to the following formulas.
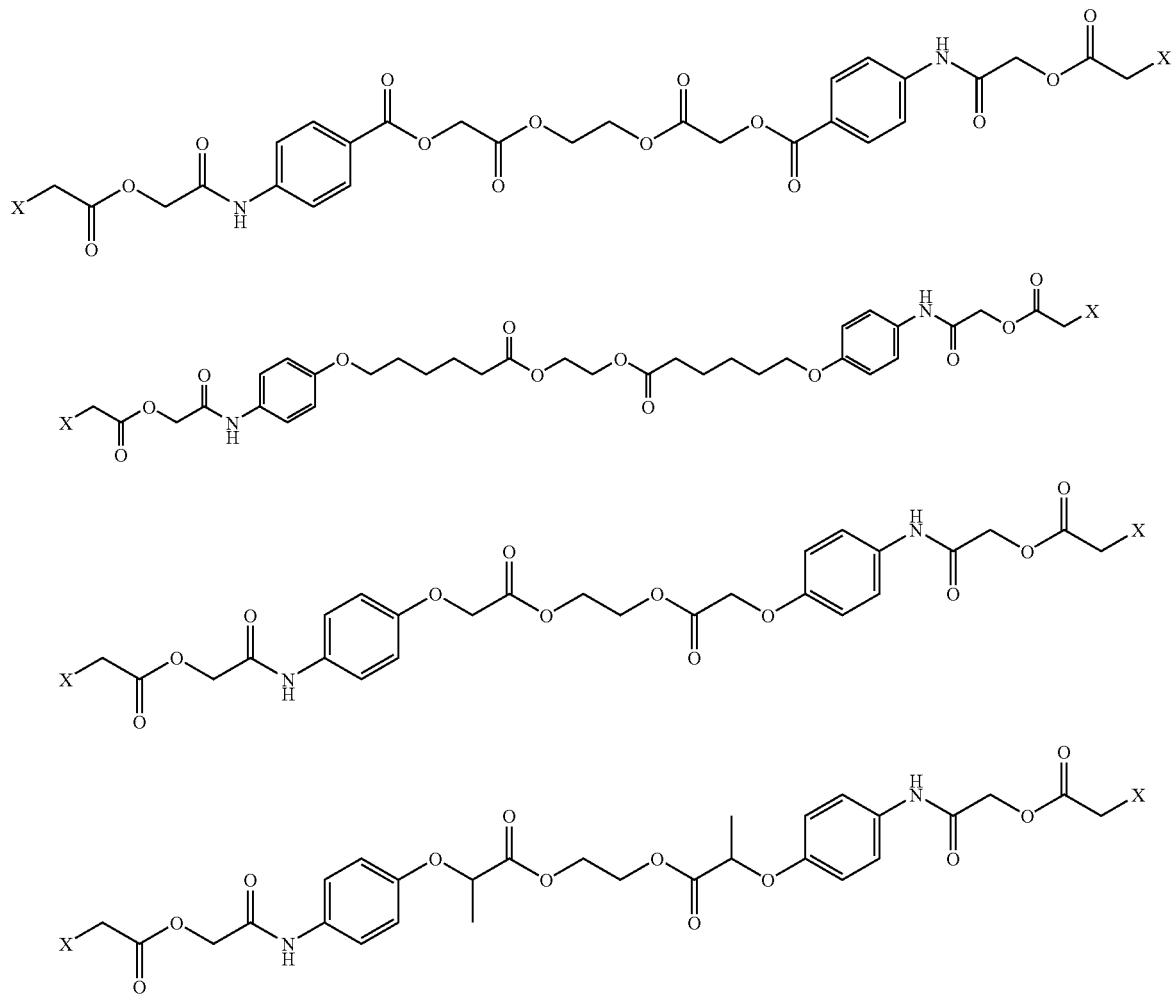

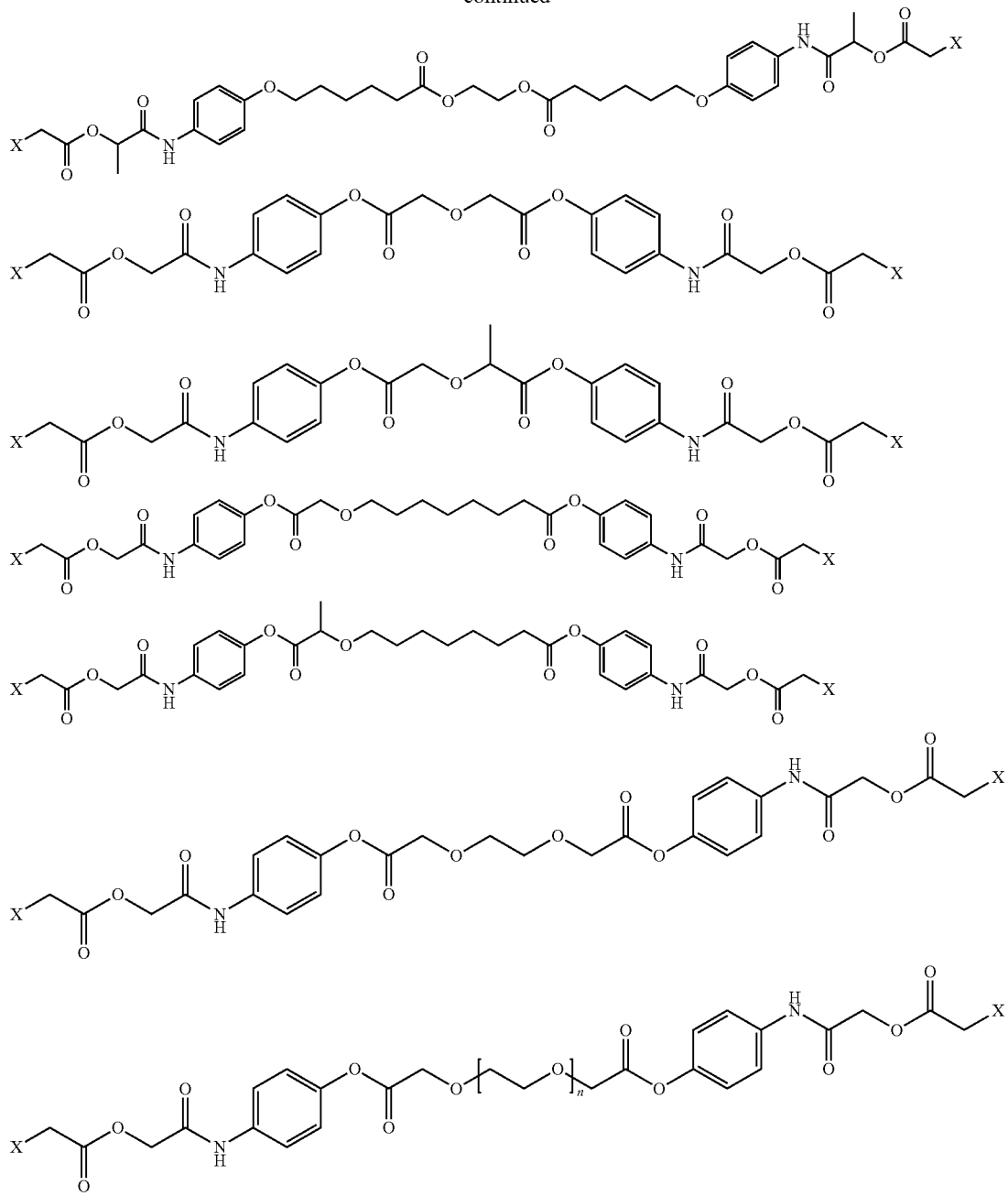

n = 10 to 12 wherein X is OH, F, Cl, Br or I and n is as previously defined.

The processes and synthetic methods described herein-throughout may be carried out in any suitable solvent. Generally, suitable solvents are solvents which are substantially non-reactive with the starting materials (reactants), the intermediates, or products at the temperatures at which the reactions are carried out, i.e., temperatures which may range from the solvent's freezing temperature to the solvent's boiling temperature, and in which the product polyesteramides are soluble. A given reaction may be carried out in one solvent or a mixture of more than one solvent. Exemplary solvents useful in the preparation of polyesteramides of Formulas I, IV, VI, and/or VIII include halogenated solvents, preferably halogenated aromatic solvents, more preferably halogenated benzene solvent, with chlorobenzene even more preferred.

One preferred embodiment of the present invention relates to bioabsorbable polyesteramides having certain nylon-like properties. Preferably the polyesteramides are formed by the condensation polymerization of tetraglycolic acid functionalized adipic acid with tetraglycolic acid functionalized hexamethylene diamine as shown below:

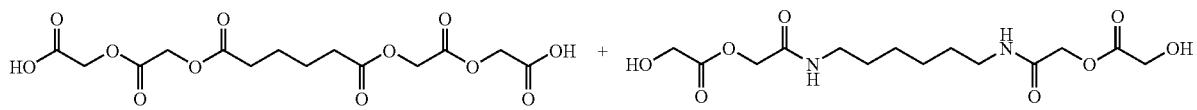

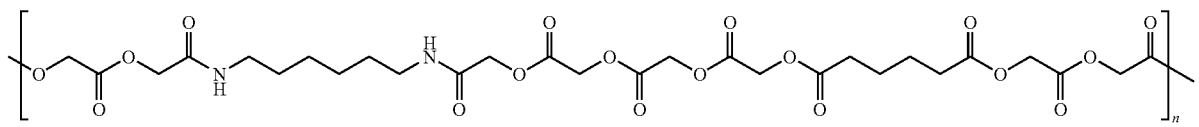

n is an integer from about 5 to about 5000, more preferably from about 10 to about 3000, still more preferably from about 20 to about 1000.

In certain preferred embodiments of polyesteramides comprising Formulas I, IV, VI, or VIII, the polyesteramide is further polymerized with a lactone monomer, preferably selected from the group consisting of glycolide, lactide, ε-caprolactone, trimethylene carbonate, and p-dioxanone. In certain preferred embodiments, the surgical articles or biodegradable packing materials of the present invention comprise these further polymerized polyesteramides.

In preferred form, the polyesteramides described herein are biodegradable and in certain aspects biocompatible and suitable for use in medicine. Such polyesteramides combine the good mechanical properties of polyamides with the degradability of polyesters.

The degradable polyesteramide herein is suitable for use in a wide variety of applications. Since the degradation products of the biocompatible polyesteramides described herein are non-toxic, they are advantageously suitable for biomedical uses. For example, the properties of the polymer may be tunable, i.e., they may be made to degrade more slowly or more quickly by reducing or increasing respectively the number of ester linkages in the polymeric chain, and can thus be utilized for fabricating short-term or long-term implantable surgical materials.

The polyesteramides may be formed into surgical articles using any know technique, such as, for example, extrusion, molding and/or solvent casting. The polyesteramides may be used alone, blended with other absorbable compositions, or in combination with nonabsorbable components. A wide variety of surgical articles may be manufactured from the polyesteramides described herein. These include but are not limited to clips and other fasteners, staples, sutures, pins, screws, prosthetic devices, wound dressings, drug delivery devices, anastomosis rings, and other implantable devices. Examples of implants include prosthetic devices, sutures, staples, clips and other fasteners, screws, pins, films, meshes, drug delivery devices or systems, anastomosis rings, surgical dressings and the like. In certain preferred drug delivery systems, the systems comprise a polyesteramide of Formula I, IV, VI, or VIII in admixture with a biologically or pharmaceutically active agent. Other preferred uses of the surgical article include their use as a scaffold for tissue engineering comprising a porous structure for the attachment and proliferation of cells. The polyesteramides herein may also be used to fabricate degradable containers and packaging materials which can degrade in landfills in contrast to existing non-degradable materials which present environmental concerns.

Fibers made from the present polyesteramides can be knitted or woven with other fibers, either absorbable or nonabsorbable to form meshes or fabrics. Compositions including these polyesteramides may also be used as an absorbable coating for surgical devices.

Optional additives which may be present in compositions made from the polyesteramides described herein include plasticizers, release agents and other processing aids. Where the composition is used to make a surgical device, stearic acid or calcium stearate are particularly useful additives due to their biocompatiblity.

In another aspect, the compositions containing the polyesteramides described herein can be used to make reinforced composites. Thus, for example, the polyesteramide composition can form the matrix of the composite and can be reinforced with bioabsorbable or nonabsorbable fibers or particles. Alternatively, a matrix of any bioabsorbable or non-bioabsorbable polymer composition can be reinforced with fibers or particulate material made from compositions containing the polyesteramides described herein.

In an alternative embodiment, the polyesteramides described herein may be admixed with a filler. The filler may be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with 100 grams of polymer. The filled, cross-linked polymers are useful, for example, as a molding composition.

It is further contemplated that one or more medico-surgically useful substances can be incorporated into compositions containing the polyesteramides described herein. Examples of such medico-surgically useful substances include, for example, those which accelerate or beneficially modify the healing process when particles are applied to a surgical repair site. For example, articles made from compositions containing the present polyesteramides may carry a therapeutic agent which will be deposited at the repair site. The therapeutic agent may be chosen for its antimicrobial properties, capability for promoting repair or reconstruction and/or new tissue growth. Antimicrobial agents such as broad spectrum antibiotic, for example, gentamycin sulfate, erythromycin or derivatized glycopeptides which are slowly released into the tissue may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet derived growth factor, macrophage derived growth factor, alveolar derived growth factor, monocyte derived growth factor, magainin, and the like. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye articles made from compositions containing the present polyesteramides in order to increase visibility of the article in the surgical field. Dyes, such as those known to be suitable for incorporation in sutures, may be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, articles in accordance with this disclosure are dyed by adding up to about a few percent and preferably about 0.2% dye to the resin composition prior to extrusion.

The compounds employed in the methods of the present invention may be prepared in a number of ways well known to those skilled in the art. The compounds may be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The following examples are included to further illustrate the invention and are not to be considered as limiting the invention anyway.

EXAMPLES

Example 1

Synthesis of Benzylacetate Functionalized Adipic Acid

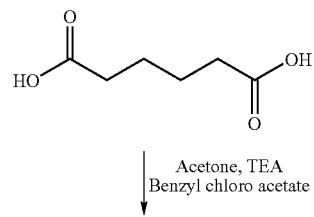

Acetone, TEA
Benzyl chloro acetate

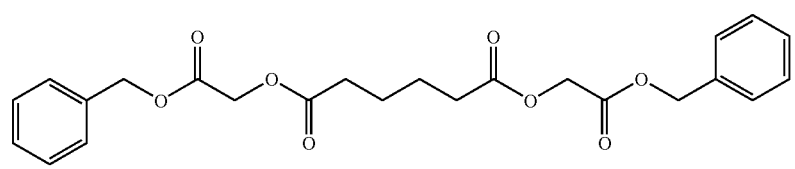

(1)

Into an oven-dried 250 ml round-bottomed flask under a nitrogen atmosphere at room temperature were added with stirring 50 grams (342 mmol) of adipic acid, 500 ml of acetone and 143 ml of triethylamine. To this solution stirring at room temperature was added dropwise 145 grams (785 mmol) of benzyl chloroacetate. The reaction mixture was stirred overnight at room temperature under nitrogen atmosphere. The progress of the reaction was monitored using thin layer chromatography. The crude product was isolated by pouring the reaction mixture into cold water and filtering the solid precipitate. The pure product was isolated with 98% purity as white powder by crystallization using ethyl acetate solvent. The solid product was characterized using HPLC and NMR spectroscopy. The purified product (1) had a melting point of 73-75° C.

Example 2

Synthesis of Glycolic Acid Functionalized Adipic Acid

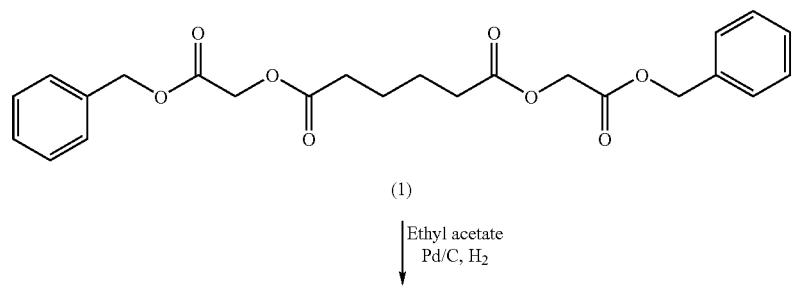

(1)

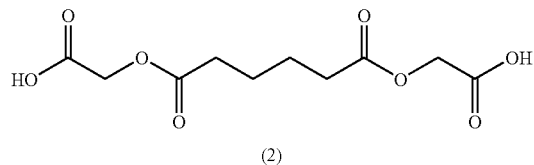

(2)

Into the flask of a Parr apparatus at room temperature was added with stirring 97 grams (219 mmol) of compound (1) in 400 ml of dry ethyl acetate. Twenty grams of palladium on charcoal catalyst (50% wet) was added. The solution was maintained in hydrogen atmosphere under pressure (4 Kg/cm²) and was shaken overnight. The progress of the reaction was monitored using thin layer chromatography. The crude product was isolated by filtering the catalyst and distilling off the ethyl acetate under vacuum. The crude solid product was taken in hexane and filtered. The isolated solid crude product was purified via crystallization in ethyl acetate. The pure product was isolated as white powder by crystallization using ethyl acetate solvent. The pure product (2) was characterized using mass spectroscopy and NMR spectroscopy. The purified product had a melting point of 108-110° C.

Example 3

Synthesis of Glycolic Acid Functionalized Hexamethylene Diamine

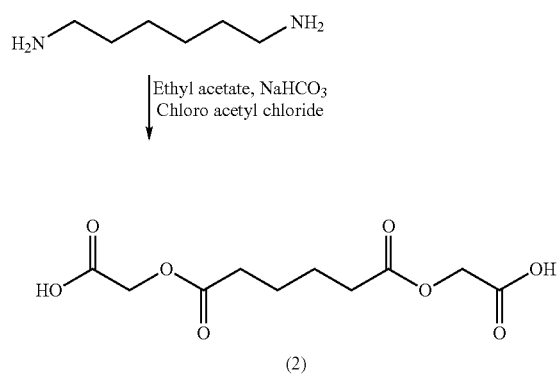

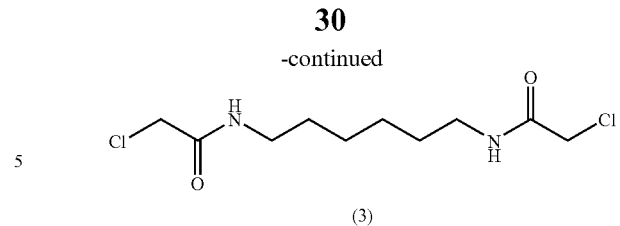

(3)

Into an oven-dried 250 ml round-bottomed flask under a nitrogen atmosphere at room temperature were added with stirring 50 grams (430 mmol) of hexamethylene diamine, 500 ml of ethyl acetate and 215 grams of sodium bicarbonate. This stirring solution was placed in an ice bath at room temperature. To this solution stirring at room temperature was added dropwise 75 ml of chloroacetyl chloride. The reaction mixture was stirred overnight at in ice bath under nitrogen atmosphere. The progress of the reaction was monitored using thin layer chromatography. The crude product was isolated by pouring the reaction mixture into cold water and filtering the solid precipitate. The pure product was isolated with 98% purity as white powder by crystallization using a (80:20) mixture of chloroform and methanol. The solid product was characterized using HPLC and NMR spectroscopy. The purified product (3) had a melting point of 130.7-132.4° C.

Example 4

Synthesis of Polyesteramide from Glycolic Acid Functionalized Hexamethylene Diamine and Glycolic Acid Functionalized Adipic Acid

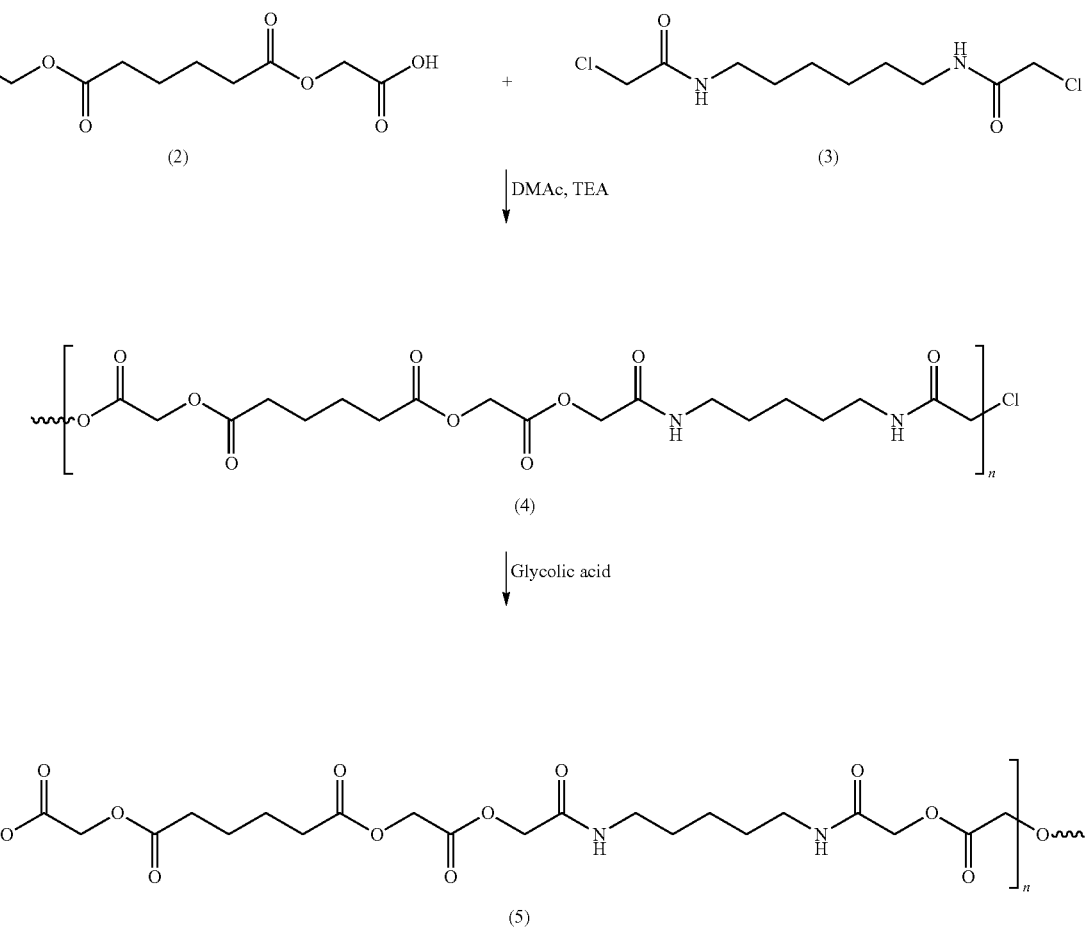

Into an oven-dried 250 ml round-bottomed flask under a nitrogen atmosphere at room temperature were added with stirring 10.00 grams of (2), 10.26 grams of (3) in 50 ml of dimethylacetamide. The solution was heated to 60° C. To this solution maintained at 60° C. was added dropwise 13.28 ml of triethylamine and the reaction mixture was left for stirring overnight at the same temperature. The progress of the reaction was monitored by the observance of the triethylamine salt. The reaction mixture was left for stirring one more night at the same temperature (60° C.). After stirring the reaction mixture for two nights, 0.5 grams of glycolic acid was further added to ensure that the polyesteramide end groups are terminated with acid group. The reaction mixture was then further left for stirring one more night. The crude product was isolated by pouring the reaction mixture into cold water followed by extraction using ethyl acetate. The final product (5) was isolated as a liquid by distilling off the ethyl acetate solvent. The final liquid product (5) was characterized using HPLC and NMR spectroscopy.

Example 5

Synthesis of Polyesteramide

Preparation of the polyesteramide described in Example 4 was repeated and the polymer solution was precipitated in cold water, and washed with Isopropyl alcohol several times followed by filtration and drying. A white powder (9 grams) with melting point of 83.5-87° C. was obtained. In vitro hydrolysis of 50 mg of this polyesteramide in 50 ml, pH 9 buffer at 100° C., resulted in complete hydrolysis in about one hour.

Example 6

Synthesis of Polyesteramide

Preparation of the polyesteramide described in Example 4 was repeated without addition of the chain terminator (glycolic acid), and the polymer solution was precipitated in cold water, and washed with isopropyl alcohol several times followed by filtration and drying. A white powder (10 grams) with melting point of 105.5-108.5° C. was obtained. In vitro hydrolysis of 50 mg of this polyesteramide in 50 ml, pH 9 buffer at 100° C., resulted in complete hydrolysis in about one hour.

Example 7

Synthesis of Hexamethylenediamine-bisglycolate

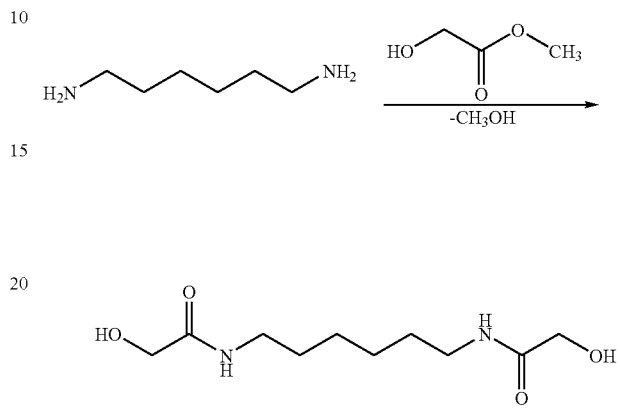

Into a three-necked, oven-dried 250 ml round-bottomed flask equipped with a short path distillation head, maintained under a nitrogen atmosphere at room temperature over a magnetic stirrer were added with stirring 11.6 grams of hexamethylenediamine and 25 grams of methyl glycolate. This stirring solution was initially heated at 80° C. and the temperature of the flask was raised to 120° C. within an hour to distill off the methanol formed during the course of reaction. After the distillation of methanol, the temperature of the flask was lowered back to room temperature. The residual crude product was purified by recrystallization from methanol to yield 17.4 grams of hexamethylenediamine-bisglycolate. The isolated solid was again recrystallized from methanol to yield a purity level greater than 99%. The re-crystallized solid had a melting point of 127° C. as determined by DSC (Differential Scanning Calorimetry).

Example 8

Synthesis of Polyesteramide Consisting of Two Glycolic Acid Units in the Polymer Repeat Unit, from Hexamethylenediamine Bis(glycolate) and Adipoyl Chloride in Chlorobenzene (N66-2G Polymer)

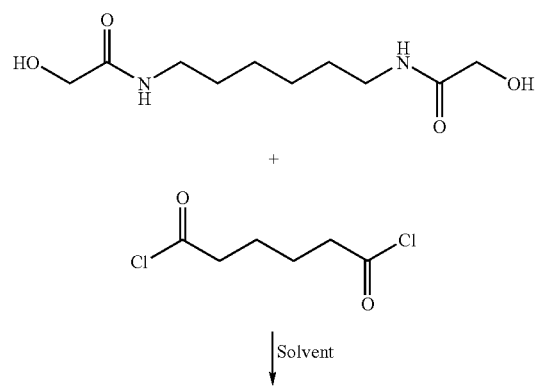

-continued

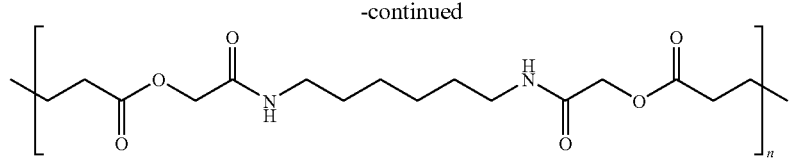

Into a three-necked, oven-dried 250 ml round-bottomed flask equipped with a dropping funnel and maintained under a nitrogen atmosphere at room temperature were added with stirring 2.32 grams of hexamethylenediamine bis(glycolate) in 150 ml of freshly distilled chlorobenzene. The reaction mixture was heated up to the refluxing temperature. Into this reaction mixture was added a solution of 1.83 grams of adipoyl chloride (dried over calcium sulfate) in 50 ml of chlorobenzene. The reaction mixture was refluxed for 4 hours until the evolution of HCl ceased, accompanied by the formation of oil clinging to the walls of the flask. The flask was cooled resulting in the solidification of oil. The chlorobenzene solvent was removed, and was followed by the addition of isopropanol and trifluoroethanol coupled with refluxing and stirring for a week to remove the solid polymer formed from the walls of the flask. The polymer was characterized using DSC and NMR spectroscopy in a mixture of $CD_2Cl_2$ containing 5 percent by wt of deuterated HFIP. The polymer was determined to have a glass transition temperature of 20° C. and a melting temperature of 124° C. Films of the polymer were prepared on pre-weighed glass slides using a (~10-20% weight/volume) solution of polymer in 2,2,2-trifluoro ethanol. Hydrolytic degradation studies of the polymer film in pH 7.4 buffer maintained at 50° C. for 24 hours resulted in approximately 3% weight loss as a result of hydrolysis.

Example 9

Synthesis of Polyesteramide Consisting of Four Glycolic Acid Units in the Polymer Repeat Unit, from Hexamethylenediamine Bis(Diglycolate) and Adipoyl Chloride in Chlorobenzene (N66-4G Polymer)

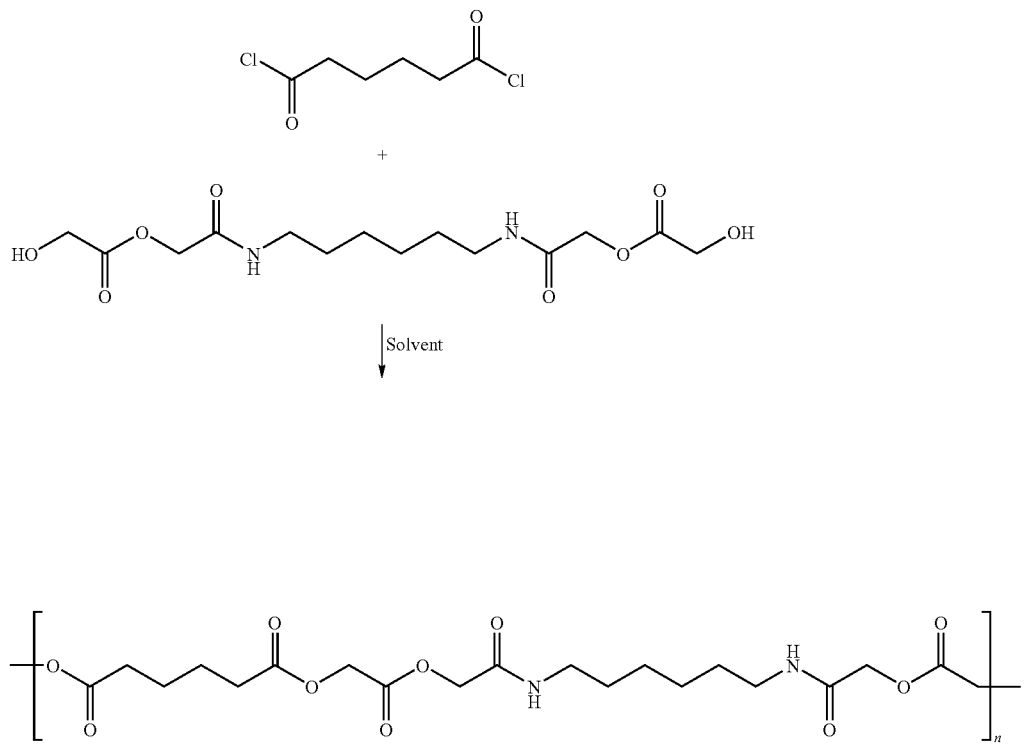

Into a three-necked, oven-dried 250 ml round-bottomed flask equipped with a dropping funnel and maintained under a nitrogen atmosphere at room temperature were added with stirring 3.48 grams of hexamethylenediamine bis(diglycolate) in 150 ml of freshly distilled chlorobenzene. The reaction mixture was heated up to 100° C. Into this reaction mixture was rapidly added a solution of 1.83 grams of adipoyl chloride (dried over calcium sulfate) in 50 ml of chlorobenzene. The reaction mixture was left for stirring overnight at 100° C. The reaction mixture was then cooled and the chlorobenzene was decanted off. The residue was allowed to cool overnight to form an off-white solid that was recovered and removed from the flask using acetone. The solid was then filtered off and dried to yield 3.8 grams of polyesteramide having four glycolic acid moieties per repeating unit of the formed polymer. DSC studies revealed that the polymer has a glass transition temperature of 17° C. and a melting temperature of 105° C. Films of the polymer were prepared on pre-weighed glass slides using a (~10-20% weight/volume) solution of polymer in 2,2,2-trifluoro ethanol. Hydrolytic degradation studies of the polymer film in pH 7.4 buffer maintained at 50° C. for 24 hours resulted in ≧95% weight loss as a result of hydrolysis.

Example 10

Hydrolytic Degradation Studies of Polyesteramides with Varying Number of Glycolic Acid Units in the Polymer Repeat Unit

TABLE 1

| Sample No. | Sample | Starting Weight of the film (mg) | % weight loss 1 Day | % weight loss 2 Days | % weight loss 6 Days |
|---|---|---|---|---|---|
| 1 | Films of Polyesteramide containing two glycolic acid units in the polymer repeat unit (N66-2G polymer) (See Example 8) | 68.0 | 3.0 | 4.5 | 25.0 |
| 2 | Films of Polyesteramide containing four glycolic acid units in the polymer repeat unit (N66-4G polymer) (see Example 9) | 67.0 | 95.0 | 100 | — |

In order to demonstrate the ability to alter the hydrolytic degradation rates of polyesteramides by modifying the number of hydroxy acid moieties per repeating unit in the polymer, films of similar weight were prepared on pre-weighed glass slides from the polymer of Example 8 and the polymer of Example 9. The films were then placed in pH 7.4 buffer maintained at 50° C. for 1, 2, and 6 days as shown above in Table 1. Films of polyesteramide containing four glycolic acid units in the polymer repeat units underwent ≧95% weight loss as a result of hydrolysis in 1 day. In contrast, films of polyesteramide containing two glycolic acid units in the polymer repeat units underwent only approximately 3% weight loss as a result of hydrolysis in 1 day. Furthermore, the film containing polyesteramide having two glycolic acid units in the polymer repeat units lost only 25% of its weight in 6 days. This experiment shows the ability to control hydrolytic degradation rate as a function of the number of glycolic acid units in the polymer repeat unit in accordance with the present invention.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A polyesteramide comprising Formula I:

—[(X—O—)$_a$—C(=O)—R$^1$—C(=O)—(O—Y)$_b$—(O—Y$^1$)$_b$—NH—R$^2$—NH—(X$^1$—O—)$_a$]$_n$—   I wherein:
 each R$^1$ and R$^2$ is independently alkylene, cycloalkylenealkylene, arylenealkylene, arylenealkylenearylene, cycloalkylenealkylenecycloalkylene, or arylenealkylenecycloalkylene, wherein:
  (1) one or more of the —CH$_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —O— or —S—; or
  (2) one or more of the —CH$_2$—CH$_2$— moieties in the alkylene chain portion of an alkylene, cycloalkylenealkylene, arylenealkylene, arylenealkylenearylene, cycloalkylenealkylenecycloalkylene, or arylenealkylenecycloalkylene moiety are optionally replaced by —C(=O)—O— or —O—C(=O)—;
 each X and X$^1$ is independently —C(=O)—CH(CH$_3$)—, —C(=O)—(CH$_2$)$_y$— or —C(=O)—(CH$_2$CH$_2$O)$_z$—CH$_2$—;
 each Y and Y$^1$ is independently —CH(CH$_3$)—C(=O)—, —(CH$_2$)$_y$—C(=O)— or —(CH$_2$CH$_2$O)$_z$—CH$_2$—C(=O)—;
 each a and b is independently an integer from about 1 to about 6;
 each y and z is independently an integer from about 1 to about 24; and
 n is an integer from about 5 to about 5000.

2. A polyesteramide of claim 1, having the formula:

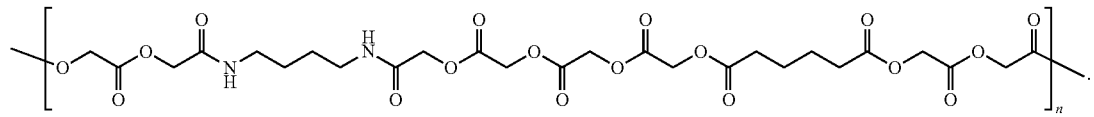

3. A surgical article comprising the polyesteramide of claim 1 or claim 2.

4. A surgical article of claim 3, wherein the polyesteramide is further polymerized with a lactone monomer.

5. A surgical article of claim 4, wherein the lactone monomer is selected from the group consisting of glycolide, lactide, ε-caprolactone, trimethylene carbonate, and p-dioxanone.

6. A surgical article of claim 3, wherein the article is a stent.

7. A surgical article of claim 3, wherein the article is a scaffold for tissue engineering comprising a porous structure for the attachment and proliferation of cells.

8. A coating for a stent, comprising the polyesteramide of claim 3.

9. A drug delivery system, comprising the polyesteramide of claim 3 physically in admixture with a biologically or pharmacologically active agent.

10. A drug delivery system of claim 9, wherein the biologically or pharmacologically active agent is physically embedded or dispersed into the polymer and the polymer is in the form of a polymeric matrix.

11. A surgical article of claim 3, wherein the article is a surgical suture.

12. A surgical article of claim 3, wherein the article is an adhesion prevention barrier film.

13. A surgical article of claim 3, wherein the article is a film, sheet, plate, clip, staple, pin, screw, or mesh.

14. A biodegradable packing material comprising the polyesteramide of claim 1 or claim 2.

15. A biodegradable packaging material of claim 1, wherein the polyesteramide has been further polymerized with a lactone monomer selected from glycolide, lactide, ε-caprolactone, trimethylene carbonate, and p-dioxanone.

16. A polyesteramide of claim 1, having the formula:

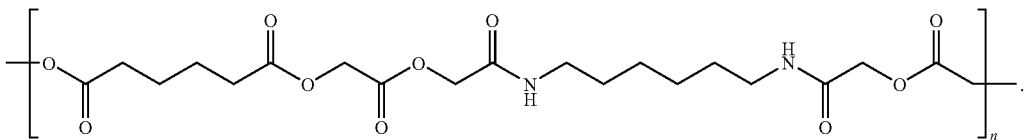

UNITED STATES PATENT AND TRADEMARK OFFICE
CERTIFICATE OF CORRECTION

PATENT NO. : 8,309,132 B2
APPLICATION NO. : 12/466709
DATED : November 13, 2012
INVENTOR(S) : Rao S Bezwada It is certified that error appears in the above-identified patent and that said Letters Patent is hereby corrected as shown below:

Column 37:
Claim 2, replace the formula below with the formula below

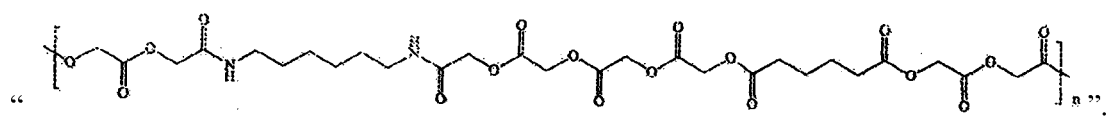

Signed and Sealed this
Twenty-second Day of January, 2013

David J. Kappos
*Director of the United States Patent and Trademark Office*